United States Patent [19]

Leonardi et al.

[11] Patent Number: 5,696,139

[45] Date of Patent: Dec. 9, 1997

[54] USE OF S-ENANTIOMERS OF 1,4-DIHYDROPYRIDINE DERIVATIVES FOR TREATING HEART FAILURE

[75] Inventors: Amedeo Leonardi, Milan; Gianni Motta, Barlassina; Rodolfo Testa, Vignate, all of Italy

[73] Assignee: Recordati S.A., Chemical and Pharmaceutical Company, Chiasso, Switzerland

[21] Appl. No.: 644,076

[22] Filed: May 9, 1996

Related U.S. Application Data

[60] Provisional application No. 60/003,509, Sep. 11, 1995.

[30] Foreign Application Priority Data

May 12, 1995 [IT] Italy ................... MI95A0956

[51] Int. Cl.$^6$ ............ C07D 211/90; C07D 413/14; A61K 31/44
[52] U.S. Cl. ............ 514/356; 514/339; 546/269.1; 546/321
[58] Field of Search ............ 546/269.1, 321; 514/339, 356

[56] References Cited

U.S. PATENT DOCUMENTS

| | | | |
|---|---|---|---|
| 4,089,969 | 5/1978 | Muchowski et al. | 424/274 |
| 4,705,797 | 11/1987 | Nardi et al. | 514/356 |
| 4,772,621 | 9/1988 | Nardi et al. | 514/356 |
| 5,091,182 | 2/1992 | Ong et al. | 424/400 |

FOREIGN PATENT DOCUMENTS

| | | |
|---|---|---|
| A 0 153 016 | 8/1985 | European Pat. Off. |
| 2847237 | 5/1980 | Germany |

OTHER PUBLICATIONS

Albertson, *Org. React.*, 12:157 (1962).
Staab et al., *Newer Methods Prep. Org. Chem.*, 5:61 (1968).
Ross, *J. Cell Bio.*, 50:172 (1971).
Ross et al., *Science* 180:1332 (1973).
Wissler et al., *Prog. Cardiovasc. Dis.*, 18:341 (1976).
Ross et al., *N. Eng. J. Med.*, 295:369 (1976).
Gimbrone, *Prog. Hemostasis Thromb.*, 3:1 (1976).
Brown et al., *J. Biol. Chem.*, 255:9344 (1980).
Brown et al., *Ann. Rev. Biochem.*, 52:233 (1983).
Edgell et al., *Proc. Natl. Acad. Sci. USA*, 80:3734 (1983).
Ross, *J. Biol. Chem.*, 259:815 (1984).
Bianchi et al., *Ircs Med. Sci.*, 14(8):817 (1986).
Schwartz et al., *Cir. Res.* 58:427 (1986).
Skalli et al., *J. Cell Bio.*, 103:2787 (1986).
Bianchi et al., *Pharmacol. Res.*, 21(2):193 (1989).
Clowes et al., *J. Cardiov. Pharmacol.*, 14:S12. (1989).
Steinberg, et al., *N. Eng. J. Med.*, 320:915 (1989).
Steinbrecher, *Curr. Opin. Lipidol.*, 1:411 (1990).
Harrison et al., *J. Lipid. Res.*, 31:2187–2193 (1990).
Wissler et al., *Ann. NY Acad. Sci.*, 598:418 (1990).
Steinberg et al., *JAMA*, 264:3047 (1990).
E.L. Bierman in *Harrison's Principle of Internal Medicine* XII Ed., p. 992 (1991).
Goldmann et al., *Agnew Chem. Int. Ed. Engl*, 30:1559 (1991).
Ylä–Herttuala, *Ann. Med.*, 23:561 (1991).
Wissler et al., *Am. J. Med.*, 91:(S1B), 1B–3S (1991).
Ashimori et al., *Chem. Pharm. Bull.*, 39:108 (1991).
Steinberg, *Circulation*, 84:1420 (1991).
Kurihara et al., *Curr. Opin. Lipidol*, 2:295 (1991).
Corsini et al., *Pharm. Res.*, 23:173 (1991).
Ishihara, *Chem. Pharm. Bull.*, 39:3236 (1991).
Doherty et al., *J. Med. Chem.*, 35:2–14 (1992).
Parthasarathy et al., *Prog. Lipid Res.*, 31:127 (1992).
Bernini et al., *Atherosclerosis*, 104:19 (1993).
De Lorenzi et al., *Chirality*, 5(8):622 (1993).
Ross, *Nature*, 362:801 (1993).
Hanna et al., *Biochem. Pharmacol.*, 45:753 (1993).
Corsini et al., *Atherosclerosis*, 101:117 (1993).
Witztum, *Lancet* 344:793 (1994).
Maggi et al., *Arteriosclerosis and Thromb.*, 14:1892 (1994).
Maggi et al., *J. Hypertension*, 13:129 (1995).
*Drugs of the Future*, 20(12):1284 (1995).

*Primary Examiner*—Zinna Northington Davis
*Attorney, Agent, or Firm*—Darby & Darby

[57] ABSTRACT

The present invention provides S-enantiomers of 1,4-dihydropyridines useful for the treatment of heart failure, preparation of compositions thereof and a method for the treatment of hypertension and heart failure comprising administration of these compounds.

9 Claims, 3 Drawing Sheets

USE OF S-ENANTIOMERS OF 1,4-DIHYDROPYRIDINE DERIVATIVES FOR TREATING HEART FAILURE

This application is a provisional application of No. 60/003,509 filed Sep. 11, 1995.

FIELD OF THE INVENTION

The present invention provides S-enantiomers of 1,4-dihydropyridines useful for the treatment of heart failure, preparation of compositions thereof and a method for the treatment of hypertension and heart failure comprising administration of these compounds.

BACKGROUND AND OUTLINE OF THE INVENTION 1,4-Dihydropyridines having calcium antagonistic activity are widely used in the treatment of several cardiovascular diseases, for example, but not limited to, hypertension and angina. An important factor which limits the use of these compounds is the negative inotropic effect exerted by some of them (S. Goldmann et al., Angew Chem. Int. Ed. Engl: 30, 1559, (1991)). This effect serves to decrease the force or energy of cardiac contractions and its presence suggests caution when administering these compounds to patients suffering from cardiac diseases (although the resulting reduction in cardiac work could be beneficial in cases where it is desirable to avoid exertion of the heart, e.g., when a patient is recovering from a coronary infarct).

Most of the 1,4-dihydropyridine derivatives used for the treatment of cardiovascular diseases, have one asymmetric carbon at the 4-position of the dihydropyridine ring. Currently, all of them are used as racemates, containing both the (S)- and the (R)-enantiomer.

Experimental evaluation of the pharmacodynamic properties of the enantiomers of several dihydropyridines (e.g.: nitrendipine, isradipine, niguldipine, nimodipine, felodipine) have shown that the (S)-enantiomer, is a more potent calcium antagonist than the corresponding (R)-enantiomer.

U.S. Pat. No. 4,705,797 and U.S. Pat. No. 4,772,621 disclose asymmetric diesters of 1,4-dihydro-2,6-dimethylpyridine-3,5-dicarboxylic acid and the stereoisomers or pharmaceutically acceptable salts thereof. These compounds are said to have antihypertensive and coronary dilating activity.

It has now been surprisingly found that, besides the known and well expected potent effect in lowering the blood pressure already shown by their racemates, the (S)-enantiomers of these compounds possess also an unexpected positive inotropic effect.

The unexpected positive inotropic effect makes the S-enantiomers particularly useful for treatment of patients afflicted by heart failure (HF). Further, this suggests the use of these compounds as the treatment of choice for patients suffering simultaneously from hypertension and compromised heart function.

Heart (or cardiac) failure is a pathophysiologic state in which an abnormality of cardiac function causes a failure of the heart to pump blood at a rate sufficient to satisfy the requirement of the metabolizing tissues. One form of cardiac failure is myocardial failure, an abnormality (insufficiency) of myocardial contraction which may be primary or secondary (e.g. can be incident to ischemia, or valvular abnormality, or pericardial inflammation or calcification). Other forms of heart failure are not accompanied by abnormal myocardial function (e.g. can be incident to acute hypertensive crisis, pulmonary embolism, or mitral valve stenosis).

The presence or absence of heart failure or more generally of inability of the heart to meet the full metabolic demand is usually assessed by heart contractility indexes measurement. Among such indexes, the maximal rate of left ventricular rise $(dp/dt_{max})$ is the method most often used to evaluate the inotropic state of the heart. In the animal models utilized to assess heart contractility, $dp/dt_{max}$ is usually derived from the ventricular pressure directly measured in the beating heart of the anaesthetized animals, usually dogs.

SUMMARY OF THE INVENTION

An object of the present invention is the use of the (S)-enantiomers of asymmetric diesters of 1,4-dihydro-2,6-dimethylpyridine-3,5-dicarboxylic acids, pharmaceutically acceptable acid addition salts thereof and pharmaceutical compositions comprising them, for the treatment of cardiac failure in mammals including humans in need of such treatment.

Accordingly one aspect of the present invention is directed to methods comprising administering to mammals in need of such treatment S-enantiomers of 1,4-dihydropyridine compounds having a positive inotropic effect for the treatment of heart failure, and compositions comprising the S-dihydropyridines. The compounds are administered in amounts sufficient to enhance myocardial contractility.

The compounds of this invention are the (S)-enantiomers of diesters of 1,4-dihydro-2,6-dimethylpyridine-3,5-dicarboxylic acids, having the general formula (I):

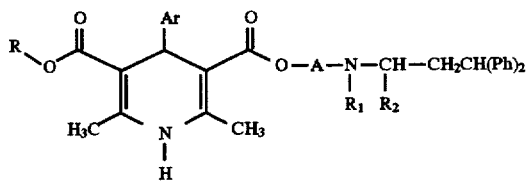

wherein:

Ph is phenyl,

Ar is: 2-nitrophenyl, 3-nitrophenyl, 2,3-dichlorophenyl or benzofurazan-4-yl,

A is a branched chain alkylene radical having from 2 to 6 carbon atoms,

R is a straight or branched chain alkyl radical having from 1 to 6 carbon atoms, optionally mono-substituted by an alkoxy substituent having from 1 to 6 carbon atoms, $R_1$ is hydrogen, hydroxy or an alkyl radical having from 1 to 4 carbon atoms, $R_2$ is hydrogen or methyl;

and pharmaceutically acceptable acid addition salts of said diesters and their hydrated or solvated form.

Preferably, R is $C_1$-$C_6$ alkyl, while $R_1$ is methyl $R_2$ is hydrogen, Ar is 3-nitrophenyl and A is branched $C_4$-$C_5$ alkyl. Most preferably, R is methyl in the combination of the preceding sentence.

Another aspect of the present invention is a process for the preparation of the S-enantiomers of the esters of formula (I), said process comprising the esterification of the (R)-enantiomer of an acid of general formula (II):

[Structure II shown: a 1,4-dihydropyridine with R-O-C(=O)- and HO-C(=O)- groups at 3,5-positions, CH₃ groups at 2,6, Ar at 4, and N-H]

wherein R and Ar have the same meaning described above, with an appropriate compound of formula (III):

$$Z-A-\underset{R_1}{N}-\underset{R_2}{CH}-CH_2CH(Ph)_2 \quad \text{III}$$

wherein Z is halogen or hydroxy and A, R₁, R₂ and Ph are as defined above.

DETAILED DESCRIPTION OF THE INVENTION

Figure 1:
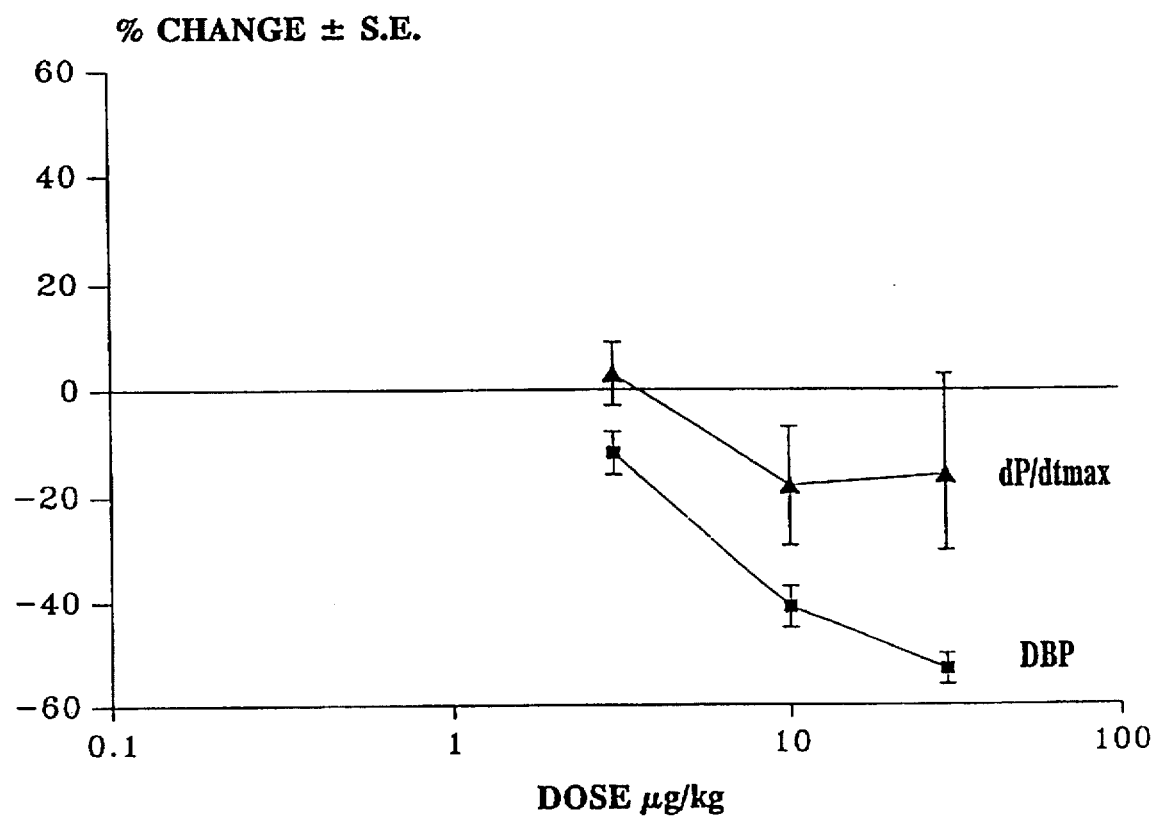
FIG. 1 shows the effects exerted on the hemodynamics parameters in the dog after administration of the racemate corresponding to Example 1.

According to the present invention the asymmetric diesters of general formula (I) may be prepared by reacting the pure (R)-enantiomer of acids of formula (II) with a compound of formula (III).

The reaction may be performed in the presence of a coupling agent (e.g.: dicyclohexylcarbodiimide, N,N'-carbonyldiimidazole or diethyl cyanophosphonate) optionally in the presence of a promoting agent (e.g.: N-hydroxysuccinimide or 4-dimethylaminopyridine) in aprotic or chlorinated solvents (e.g.: N,N-dimetylformamide or chloroform) at temperatures ranging from −10° to 140° C. according to well known synthetic methods: Albertson, Org. React. 12, 205–218 (1962); Doherty et al., J. Med. Chem. 35, 2 (1992); Staab et al., Newer Methods Prep. Org. Chem. 5, 61 (1968); Ishihara, Chem. Pharm. Bull. 39, 3236 (1991).

Alternatively, the compounds of formula (I) may be prepared by first reacting the (R)-enantiomer of the above acid intermediates (II) with alkyl chloroformate in presence of a tertiary amine (e.g. triethylamine), then adding the intermediate (III) at 0°–80° C. Optionally, a promoting agent (e.g., 1-hydroxypiperidine) may be added before the intermediate (III) addition, see Albertson, Org. React. 12, 157 (1962).

The compounds of the invention may also be prepared by conversion of the (R)-enantiomer of the acid intermediates (II) into the corresponding acyl halide using inorganic acid halides (e.g., phosphorous pentachioride or thionyl chloride) in a chlorinated solvent (e.g., chloroform, dichloroethane, dichloromethane or 1,1,1-trichloroethane), optionally in the presence of promoting agents (e.g., N,N-dimethylformamide) at temperatures ranging between −10° and 65° C. Said acyl halides may or may not be isolated before the addition of the intermediate (III).

The homo-chiral (S)-enantiomers of diesters of general formula (I) so obtained, may be purified according to methods known in the art, either as base (e.g.: by column chromatography) or as salts (e.g.: by re-precipitation or recrystallization).

The pharmaceutically acceptable salts of the chiral diesters may be prepared from the free bases in conventional manner.

Preferred pharmaceutically acceptable acid addition salts are those of hydrochloric, sulfuric, maleic, succinic, citric, methanesulfonic and toluenesulfonic acids without limitation.

The compounds of the present invention, the S-enantiomers, may be administered orally, parenterally or rectally in pharmaceutical preparations which comprise the active compound in combination with pharmaceutically acceptable carriers.

Carriers can be solid, semisolid or liquid diluents as well as capsules and may optionally provide modified release of the active drug. The selection of the most suitable carriers will depend on the administration route. For example, a preparation to be administered orally, in form of tablets, can include, in addition to the active substance, solubilizers (e.g.: a polyethoxylated fatty acid), components which modify the drug release (e.g.: hydroxypropylmethyl cellulose), fillers (e.g.: lactose), binders (e.g.: hydroxypropylmethyl cellulose) and/or lubricants (e.g.: sodium stearylfumarate).

The tablets can be coated with suspensions of coloring pigments (e.g.: iron oxide) and film forming agents (e.g.: cellulose derivative).

Aqueous solutions of the drug for parenteral use can include co-solvents (e.g.: polyethylene glycol).

Usually the amount of the active compound ranges between 0.1 and 99% by weight of the total formulation, preferably between 0.5 and 20% by weight in formulations for injection and between 2 and 50% by weight in formulations for oral administration:

An effective amount of a compound having formula I, for increasing contractility of the head muscle is an amount of the compound which is effective to lower the diastolic blood pressure about 20% to about 30%. The daily dose of the active compound depends on individual needs (e.g.: the patient's condition, body weight, age or sex etc.) as well as on the administration route. Generally, the oral dosage may range from 0.1 to about 100 mg, preferably from about 1 to about 20 mg, of active compound per mammal (including human) per day.

The S-enantiomers of the present invention were tested in vivo in a dog model, in comparison with the corresponding racemates at different doses in order to assess their pharmacological activity. Percent changes on diastolic blood pressure (DBP) and the cardiac contractility were detected. The results show the high vascular selectivity of the S-enantiomers and the positive inotropic effect on the head contractility. Both the effects indicate a potential use of these compounds as therapeutic agents for the treatment of head failure.

To further illustrate the present invention and the advantages thereof, the following specific examples are given, it has to be understood that they are intended only as illustrative and not limitative.

EXAMPLE 1

(S)-(+)-methyl 1,1,N-trimethyl-N-(3,3-diphenylpropyl)-2-aminoethyl 1,4-dihydro-2,6-dimethyl-4-(3-nitrophenyl)pyridine-3,5-dicarboxylate hydrochloride. 0.5 H₂O.

Thionyl chloride 0.13 mL was added, at −10° C., to a stirred suspension of 0.54 g of (R)-(−)-1,4-dihydro-2,6- dimethyl-4-(3-nitrophenyl)-5-methoxycarbonylpyridine-3-carboxylic acid (prepared as described in A. Ashimori et al., Chem. Pharm. Bull. 39., 108–111, (1991)) in 2.9 mL of anhydrous dichloromethane and 0.75 mL of anhydrous N,N-dimethylformamide kept under nitrogen atmosphere and sheltered from the direct light. After 1 h at 0° C., a solution of 0.48 g of 2,N-dimethyl-N-(3,3-diphenylpropyl)-1-amino-2-propanol, (prepared as described in U.S. Pat. No. 4,772,621), in 1 mL of dichloromethane was added at −5° C. After stirring for 3 hours at 0° C. and standing overnight at 20°–25° C., the solvent was evaporated in vacuo and the residue was dissolved in 20 mL of ethyl acetate. The organic phase was washed sequentially with brine (4 mL), 10% aqueous sodium carbonate solution (5×4 mL), brine (4 mL), 1N hydrochloric acid (5×5 mL), brine (4 mL), 10% aqueous sodium carbonate solution (2×5 mL) and finally with brine (4 mL). The organic phase was dried over anhydrous sodium sulfate and evaporated to dryness in vacuo. The residue was purified by flash chromatography on silica gel column eluting with petroleum ether-acetone 85:15. The unitary TLC fractions (petroleum ether—acetone 7:3 by volume and chloroform—5N methanolic ammonia 99:21.1 by volume) were evaporated to give a residue that was dissolved in 75 mL of diethyl ether containing 3% of acetone. After filtration the solution was acidified with 3N ethereal hydrogen chloride and the precipitate was collected by suction and dried at 78° C./15 mmHg to give 0.66 g of the title compound. M.p. 115°–125° C.; $[\alpha]_D^{25}=+70.56°$ (MeOH, c=0.981).

Elemental analysis % for $C_{36}H_{41}N_3O_6 \cdot HCl \cdot 0.5\ H_2O$: Found: C, 65.47; H, 6.57; N, 6.29; Cl, 5.32; $H_2O$, 1.68. Calcd.: C, 65.79; H, 6.60; N, 6.39; Cl, 5.39; $H_2O$, 1.37.

$^1$H-NMR Spectrum of the base at 200 MHz (CDCl$_3$, (δ)):

| 8.10 | (m, 1H) | nitrophenyl, CH in 2 |
|---|---|---|
| 7.97 | (m, 1H) | nitrophenyl, CH in 4 |
| 7.62 | (m, 1H) | nitrophenyl, CH in 6 |
| 7.33 | (dd, 1H) | nitrophenyl, CH in 5 |
| 7.29–7.10 | (m, 10H) | H aromatics of benzhydryl |
| 5.79 | (bs, 1H) | pyridine, NH |
| 5.05 | (s, 1H) | pyridine, CH in 4 |
| 3.92 | (t, 1H) | benzhydryl CH |
| 3.63 | (s, 3H) | COOCH$_3$ |
| 2.57 | (m, 2H) | OC(CH$_3$)$_2$CH$_2$N |
| 2.40–2.23 | (m, 2H) | N(CH$_3$)CH$_2$CH$_2$ |
| 2.33/2.27 | (2s, 6H) | pyridine, CH$_3$ in pos. 2 and 6 |
| 2.19–2.09 | (m, 2H) | N(CH$_3$)CH$_2$CH$_2$ |
| 2.17 | (s, 3H) | NCH$_3$ |
| 1.35/1.31 | (2s, 6H) | OC(CH$_3$)$_2$CH$_2$N |

EXAMPLE 2

2,2,N-trimethyl-N-(3,3-diphenylpropyl)-1-amino-3-propanol hydrochloride

A mixture comprising N-methyl-3,3-diphenylpropylamine hydrochloride (2.61 g) (prepared as described in DE 935,468), acetic anhydride (1 mL) and formaldehyde (37% in water; 0.9 mL), was refluxed for 30 minutes. Then a solution of isobutyraldheyde (1 mL) in acetic anhydride (1 mL) was added dropwise and the mixture was maintained at reflux temperature for further 30 minutes. The solvent was then evaporated under vacuum and the residue dissolved in water, alkalinized and extracted with diethyl ether. The organic layer, was separated, dried and, after evaporation of the solvent, the residue was purified by silica-gel chromatography eluting with methylene chloride/methanol (98:2 to 96:4). Pure fractions were collected and the solvent was evaporated to give the Mannich base N-(3,3-diphenylpropyl)-N,2,2-trimethyl-3-aminopropanaldehyde (Compound a) (1.55 g), which was characterized by NMR spectrometry.

$^1$H-NMR at 60 MHz (CDCl$_3$, (δ)):

| 9.5 | (s, 1H) | CHO |
|---|---|---|
| 7.3 | (s, 10H) | aromatics |
| 4.0 | (t, 1H) | Ph$_2$—CH |
| 2.7–1.9 | (m, 9H) | 3 CH$_2$ and NCH$_3$ |
| 1.0 | (s, 6H) | C(CH$_3$)$_2$ |

Sodium borohydride (0.25 g) was added at ⅔° C. to a solution of 1.5 g of compound a) in methanol (7 mL) cooled at ⅔° C. for 30 minutes, and then at room temperature for 1 hour. The resulting solution was poured in 35 mL of water, the crude was extracted with diethyl ether and the organic layer was separated and extracted with a solution of oxalic acid (0.6 g in 35 mL of water). The aqueous acidic solution, washed twice with diethyl ether, made alkaline with 30% sodium hydroxide (1 mL) was then extracted with diethyl ether. To the ethereal solution, after drying over sodium sulphate, was added HCl in diethyl ether and the crude hydrochloride was collected by filtration and crystallized from acetone to give 1.26 g of the title product melting at 147°–148° C.

$^1$H-NMR at 60 MHz (CDCl$_3$, (δ)):

| 10.8–9.9 | (m, 1H) | NH$^+$ |
|---|---|---|
| 7.7–7.2 | (m, 10H) | aromatics |
| 5.0–4.4 | (m, 1H) | OH |
| 4.1 | (t, 1H) | Ph$_2$—CH |
| 3.7 | (s, 2H) | CH$_2$O |
| 3.5–2.5 | (m, 9H) | 3 CH$_2$ and NCH$_3$ |
| 1.1 | (s, 6H) | C(CH$_3$)$_2$ |

EXAMPLE 3

(S)-(+)-methyl 2,2,N-trimethyl-N-(3,3-diphenylpropyl)-3-aminopropyl 1,4-dihydro-2,6-dimethyl-4-(3-nitrophenyl)pyridine-3,5-dicarboxylate hydrochloride. 0.7 H$_2$O The title compound was prepared according to the method described in Example 1, using 2,2,N-trimethyl-N-(3,3-diphenylpropyl)-1-amino-3-propanol, prepared as described in Example 2, instead of 2,N-dimethyl-N-(3,3-diphenylpropyl)-1-amino-2-propanol. The crude product was purified by flash chromatography on silica gel column eluting with n-hexane-ethyl acetate gradient from 70:30 to 65:35. The fractions containing the pure base were pooled, the solvents were evaporated in vacuo to dryness, and the residue was dissolved in diethyl ether. After filtration the solution was acidified with 3 N ethereal hydrogen chloride and the precipitate was collected by vacuum filtration and dried at 78° C./15 mmHg to give the title compound, m.p. 116°–127° C.

$^1$H-NMR Spectrum at 200 Mhz (CDCl$_3$, (δ)):

| 11.20–11.55 | (bs, 1H) | NH$^+$ |
|---|---|---|
| 8.06 | (dd, 1H) | nitrophenyl, CH in 2 |
| 7.90–8.03 | (m, 1H) | nitrophenyl, CH in 4 |
| 7.60–7.45 | (dd, 1H) | nitrophenyl, CH in 6 |
| 7.10–7.45 | (m, 11H) | nitrophenyl, CH in 5 and benzhydryl aromatic H's |
| 6.68–6.82 | (d, 1H) | pyridine, NH |
| 5.07 | (d, 1H) | pyridine, CH in 4 |

| | | |
|---|---|---|
| 3.85–4.15 | (m, 3H) | benzhydryl CH and COOCH$_2$ |
| 3.67 | (s, 3H) | COOCH$_3$ |
| 2.50–3.15 | (m, 9H) | CH$_2$N(CH$_3$)CH$_2$CH$_2$CH |
| 2.34/2.41 | (2d, 6H) | pyridine, CH$_3$ in pos. 2 and 6 |
| 1.70 | (bs, 1.4H) | H$_2$O |
| 0.98/1.18 | (2d, 6H) | CH$_2$C(CH$_3$)CH$_2$ |

EXAMPLE 4

Pharmacological tests

The (S)-enantiomers prepared in Examples 1 and 3 were tested for their in vivo pharmacological activity in a dog model, and compared to the racemate of compound of Example 1.

Male beagle dogs weighing 11–13 kg, 12 months old, from Green-Hill and Morini Allevamenti (Italy), were used. All dogs were anaesthetized with sodium pentobarbital (30 mg/kg i.v. for induction and 2 mg/kg/hour i.v. for maintenance), and artificially ventilated with a pump via a cuffed endotracheal tube.

Intraventricular and arterial blood pressure were monitored by means of a Millar Mikro-Tip catheter with two pressor sensors inserted in the left ventricle via left common carotid artery. The right femoral vein was cannulated to allow drug infusion. The following parameters were evaluated: systolic (SBP), diastolic (DBP) and mean (MBP) blood pressure, left ventricular systolic pressure (LVP) and first derivative of LVP, dP/dt max as an index of cardiac contractility. The compounds were tested at the following dosages (intravenously administered in cumulative manner):

| Compound | Dose (µg/kg) |
|---|---|
| Racemate corresponding to Example 1 | 3, 10, 30 |
| Example 1 | 0.5, 1, 3, 5 |
| Example 3 | 1, 3, 5, 10 |

Figure 2:
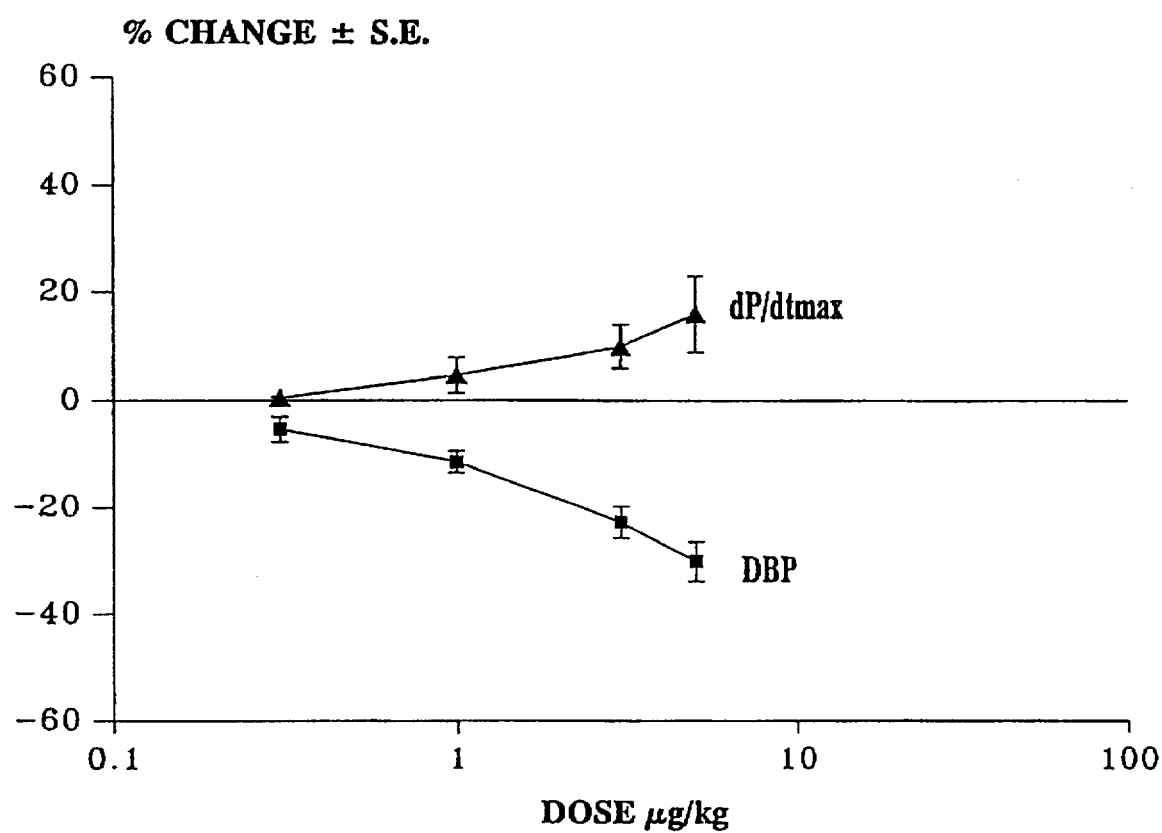
FIG. 2 shows the effects exerted on the hemodynamics parameters in the dog after administration of the (S)-enantiomer prepared in Example 1.
Figure 3:
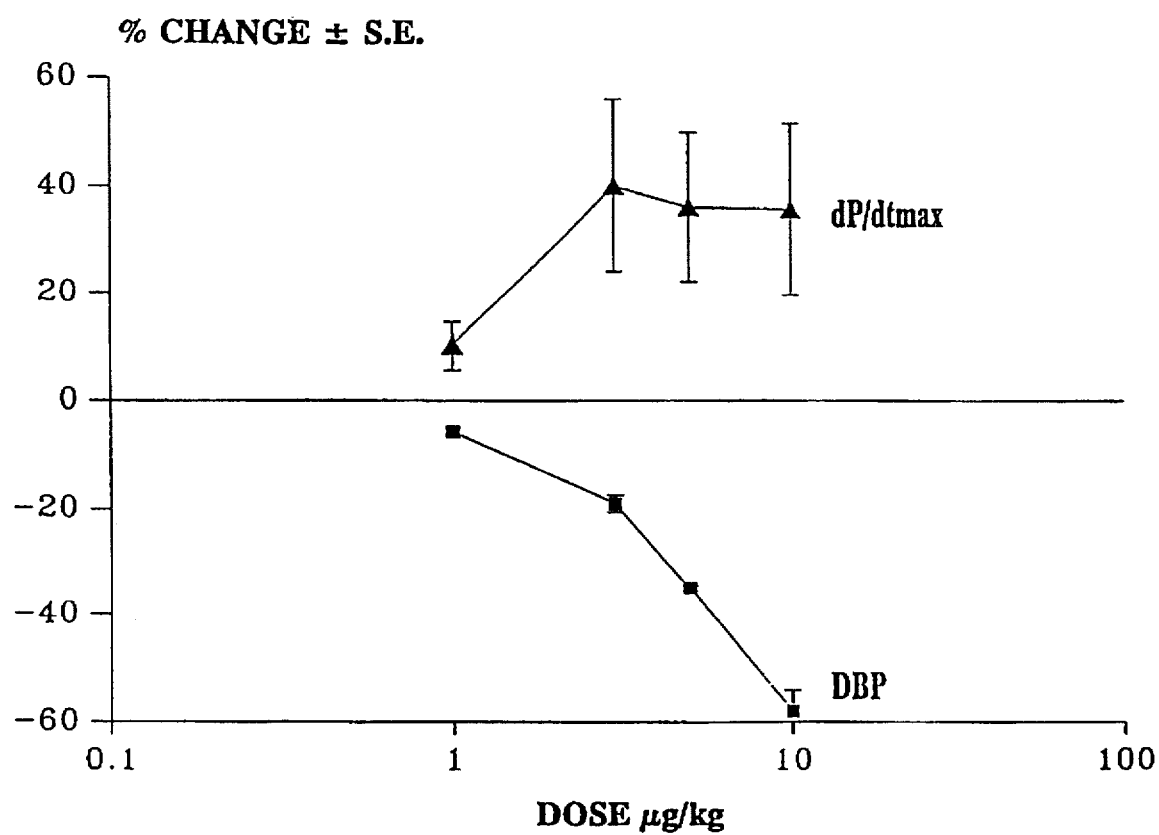
FIG. 3 shows the effects exerted on the hemodynamics parameters in the dog after administration of the the (S)-enantiomer prepared in Example 3.

The results are reported in FIGS. 1–3. The percent changes on diastolic blood pressure (DBP) and cardiac contractility, at the different doses tested, are shown. In particular, FIGS. 1, 2 and 3 show the effects exerted on the hemodynamics parameters in the dog by: the racemate corresponding to Example 1, the (S)-enantiomer of Example 1 and the (S)-enantiomer of Example 3 respectively.

FIG. 1 clearly shows that the racemate corresponding to the compound of Example 1 has a potent blood pressure lowering effect (DBP) accompanied by a slight reduction of cardiac contractility (dP/dt max).

In contrast, FIGS. 2 and 3 show that the noticeable blood pressure lowering effects of compounds of Examples 1 and 3 are associated with an increase of dP/dt max. The increase in the dP/dt max illustrates the positive inotropic effect.

The invention has been described above by reference to preferred embodiments but, as those skilled in the art will appreciate, many additions, omissions and modifications are possible all within the scope of the claims below.

All patents and literature references cited in this specification are hereby incorporated by reference in their entirety. In case of inconsistencies, the present description, including the definitions and interpretations, will prevail.

We claim:

1. A method for the treatment of heart failure comprising administering to a patient in need of said treatment an amount effective for increasing contractility of the heart muscle of an isolated or purified S-enantiomer of a compound having the formula I:

$$R\diagdown O \diagdown C(=O) \diagdown \cdots \diagdown C(=O) \diagdown O-A-N(R_1)-CH(R_2)-CH_2CH(Ph)_2 \qquad I$$

wherein:

Ph is phenyl,

Ar is: 2-nitrophenyl, 3-nitrophenyl, 2,3-dichlorophenyl or benzofurazan-4-yl,

A is a branched chain alkylene radical having from 2 to 6 carbon atoms,

R is a straight or branched chain alkyl radical having from 1 to 6 carbon atoms, optionally mono-substituted by an alkoxy substituent having from 1 to 6 carbon atoms, R$_1$ is hydrogen, hydroxy, or an alkyl radical having from 1 to 4 carbon atoms, R$_2$ is hydrogen, or methyl;

or a pharmaceutically acceptable acid addition salt thereof, optionally in hydrated or solvated form.

2. The method of claim 1, wherein the compound having formula I is selected from the group consisting of: (S)-(+)-methyl 1,1,N-trimethyl-N-(3,3-diphenylpropyl)-2-aminoethyl 1,4-dihydro-2,6-dimethyl-4-(3-nitrophenyl) pyridine-3,5-dicarboxylate; and (S)-(+)-methyl 2,2,N-trimethyl-N-(3,3-diphenylpropyl)-3-aminopropyl 1,4-dihydro-2,6-dimethyl-4-(3-nitrophenyl)pyridine-3,5-dicarboxylate.

3. The method of claim 1 wherein R$_1$ is methyl, R$_2$ is hydrogen, Ar is 3-nitrophenyl and A is a branched alkyl group having 4 or 5 carbon atoms.

4. The method of claim 1, wherein R is methyl, A is 3-nitrophenyl, R$_2$ is methyl and R$_2$ is hydrogen.

5. The method of claim 1, wherein A is —C(CH$_3$)$_2$—CH$_2$— or —CH$_2$—C(CH$_3$)$_2$—CH$_2$—.

6. The method of claim 1, wherein the compound having formula I comprises:

(S)-(+)-methyl 1,1,N-trimethyl-N-(3,3-diphenylpropyl)-2-aminoethyl 1,4-dihydro-2,6-dimethyl-4-(3-nitrophenyl) pyridine-3,5-dicarboxylate.

7. The method of claim 1, wherein the compound having formula I comprises:

(S)-(+)-methyl 2,2,N-trimethyl-N-(3,3-diphenylpropyl)-3-aminopropyl 1,4-dihydro-2,6-dimethyl-4-(3-nitrophenyl) pyridine-3,5-dicarboxylate hydrochloride.

8. The method of claim 1, wherein the dosage of active compound is from 0.1 to about 100 mg, per day.

9. The method of claim 1, wherein the dosage of active compound is from about 1 to about 20 mg, per day.

* * * * *